(12) United States Patent
Freire Torres Russo et al.

(10) Patent No.: US 9,169,218 B2
(45) Date of Patent: *Oct. 27, 2015

(54) COMPOUNDS AND PHARMACEUTICAL COMPOSITIONS FOR TREATING DISORDERS ASSOCIATED WITH THE 5-HT1A AND 5-HT2A RECEPTORS

(71) Applicants: ACHÉ LABORATÓRIOS FARMACÊUTICOS S.A., Guarulhos (BR); ACHÉ INTERNATIONAL (BVI) LTD., Tortola (VG)

(72) Inventors: Valter Freire Torres Russo, Itapira (BR); Elisa Mannochio De Souza Russo, Itapira (BR)

(73) Assignees: ACHE LABORATORIOS FARMACEUTICOS S.A., Sao Paul (BR); ACHE INTERNATIONAL (BVI) LTD., Tortola (VG)

( * ) Notice: Subject to any disclaimer, the term of this patent is extended or adjusted under 35 U.S.C. 154(b) by 0 days.

This patent is subject to a terminal disclaimer.

(21) Appl. No.: 14/227,313

(22) Filed: Mar. 27, 2014

(65) Prior Publication Data
US 2014/0303179 A1 Oct. 9, 2014

Related U.S. Application Data

(62) Division of application No. 13/824,063, filed as application No. PCT/BR2011/000374 on Sep. 22, 2011, now Pat. No. 8,735,578.

(30) Foreign Application Priority Data

Sep. 24, 2010 (BR) ...................................... 1003506

(51) Int. Cl.
| | |
|---|---|
| A61K 31/497 | (2006.01) |
| C07D 239/88 | (2006.01) |
| C07D 239/90 | (2006.01) |
| A61K 31/513 | (2006.01) |
| A61K 31/517 | (2006.01) |

(52) U.S. Cl.
CPC ............ *C07D 239/88* (2013.01); *C07D 239/90* (2013.01); *A61K 31/513* (2013.01); *A61K 31/517* (2013.01)

(58) Field of Classification Search
None
See application file for complete search history.

(56) References Cited

U.S. PATENT DOCUMENTS 4,841,051 A * 6/1989 Shiozawa et al. ............. 544/287

OTHER PUBLICATIONS

Marek et al., Neuropsychopharmacology, 2003, 28, 402-412.*
Meston et al., Current Opinion in Urology, 2001, 11, 603-609.*

* cited by examiner

*Primary Examiner* — Dennis Heyer
*Assistant Examiner* — Daniel M Podgorski
(74) *Attorney, Agent, or Firm* — B. Aaron Schulman, Esq.; Stites & Harbison, PLLC.

(57) ABSTRACT

This invention is related to the alkyl-piperazine-phenyl 4 (3H)-quinazolinones general formula (I) compounds, pharmacologicaly active and able to act on the 5-$HT_{1A}$ and 5-$HT_{2A}$ serotonin receptors in a manner that promotes the control, relief or cure of disorders associated with these receptors, and pharmaceutical compositions containing the compounds for the treatment of disorders associated with these receptors. These compounds and their pharmaceutical compositions are useful in the treatment of conditions such as depression, anxiety, phobias, addictions, aggressiveness, impulsiveness, panic, psychotic, eating and sleep disorders, obsessive-compulsive disorder and female sexual dysfunctions, among other disorders associated with these receptors.

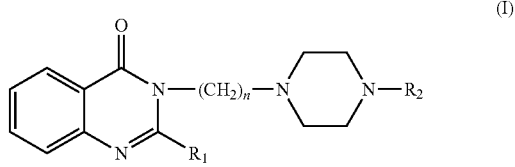

(I)

8 Claims, 1 Drawing Sheet

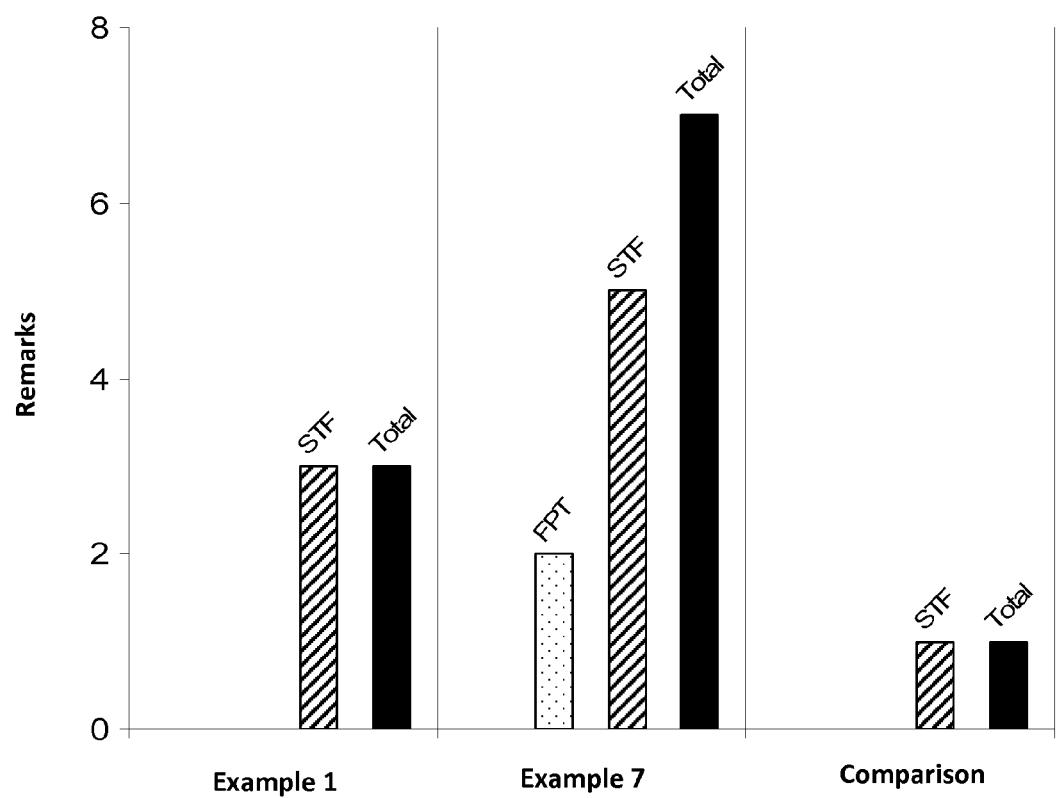

COMPOUNDS AND PHARMACEUTICAL COMPOSITIONS FOR TREATING DISORDERS ASSOCIATED WITH THE 5-HT1A AND 5-HT2A RECEPTORS

CROSS REFERENCE TO RELATED APPLICATIONS

This application is a divisional application of U.S. patent application Ser. No. 13/824,063, having a filing date of Mar. 19, 2013, which is a National Stage Application of PCT/BR2011/000374, filed Sep. 22, 2011, all of said applications incorporated herein by reference.

FIELD OF THE INVENTION

This invention is related to the alkyl-piperazine-phenyl 4 (3H)-quinazolinone compounds, which are pharmacologicaly active and able to interact with the 5-$HT_{1A}$ and 5-$HT_{2A}$ serotonin receptors promoting the control, relief or cure of disorders associated with these receptors and pharmaceutical compositions containing the compounds. This invention is also related to the use of these compounds in the treatment of depression and anxiety disorders, phobias, addictions, aggressiveness, impulsiveness, panic, eating, sleep and psychotic disorders, obsessive-compulsive disorder, female sexual dysfunctions, among others disorders associated with the 5-$HT_{1A}$ and 5-$HT_{2A}$ serotonin receptors.

BACKGROUND OF THE INVENTION

Selective Serotonin Reuptake Inhibitors (SSRI) constitute the class of medications that are currently most widely used for the treatment of depression and anxiety disorders, obsessive-compulsive disorder, phobias, social phobia and panic.

These drugs act on the serotonin transporter, a protein integrated with the membrane whose function is to transport the neurotransmitter—serotonin—from the synaptic spaces to the interior of the pre-synaptic neurons. Its inhibition by the SSRIs triggers an increase in the serotonin concentration in the synapses, resulting in greater availability of this neurotransmitter for binding with the serotonin receptors of the contiguous neurons, with the consequent propagation of the nerve impulse. Although the SSRIs extend the availability of serotonin in the synapses, this neurotransmitter is not specific for binding with the different existing serotonin receptors.

At the moment, seven families or populations of serotonin receptors are known, classified from 5-$HT_1$ to 5-$HT_7$ on the basis of their different structural and operating characteristics. Multiple subpopulations or subtypes (homologous types and conjugated variants) exist for each of these families. While some subtypes have been targeted by many studies allowing their characterization in structural and functional terms, the function of other subtypes have not yet been fully elucidated (*Psychopharmacology*—4th *Generation—Serotonin Receptors, Subtypes and Ligands*—Glennon et al, available at: http://www.acnp.org/g4/GN401000039/Ch039.html).

In addition to interacting with the serotonin transporter, serotonin interacts indistinctly with all the populations and the respective subpopulations of the serotonin receptors. If on the one hand the increase on the concentration of serotonin has a positive therapeutic effect that is appropriate for treating certain dysfunctions, on the other side this increase prompts the appearance of undesired side effects, probably resulting from the indiscriminate activation of non-specific receptors that are not related to the disorders being treated.

Several studies describe the importance of the 5-$HT_{1A}$ agonism, with the activation of these receptors being particularly relevant for the treatment of depression and anxiety disorders, phobias, panic impulsiveness, obsessive-compulsive disorder, among others. Some drugs have been developed, specifically targeting these receptors. This is the case of buspirone and tandospirone which, although serving as partial agonists, target only the 5-$HT_{1A}$ receptors, not presenting any significant affinity for other serotonin receptors.

Although these drugs target the 5-$HT_{1A}$ receptors whose activation is acknowledged as important in the treatment of these various disorders, they are not rated as first choice drugs, mainly because their effects in the treatment of depression and other associated disorders are significantly less than those presented by the SSRIs. Among the hypotheses presented to explain this behavior, or deficiency of activity, is the fact that they act as partial agonists with these receptors. In fact, the mechanism of action of buspirone occurs through the agonism of the pre-synaptic 5-$HT_{1A}$ receptors, while it acts together with the post-synaptic 5-$HT_{1A}$ receptors as a partial agonist (*The American Psychiatric Publishing Textbook of Psychopharmacology*, 4th Edition, Chap. 25—*Buspirone and Gepirone*—edited by Alan F. Schatzberg and Charles B. Nemeroff).

Recent studies indicate that 5-$HT_{1A}$ and 5-$HT_{2A}$ receptors are particularly involved in disorders related to depression and anxiety. While the agonism of the 5-$HT_{1A}$ receptors seems to have a favorable therapeutic effect in the treatment these disorders, the antagonism of the 5-$HT_{2A}$ receptors seems to be responsible for triggering a similar effect. Thus, it is believed that the therapeutic effect arising from the agonism of the 5-$HT_{1A}$ receptors is partially neutralized should the substance promote in parallel the agonism of the 5-$HT_{2A}$ receptors, indicating the possible existence of a functional antagonism between the two receptors (Marek et al in *Neuropsychopharmacology* (2003) 28: 402-412; Celada et al in *J. Psychiatry Neurosci.* (2004) 29 (4): 252-265).

The long latency period between the start of the treatment and the appearance of the initial effects noted in patients being treated with the SSRIs, may be associated at least partially with the increased concentration of serotonin available to the 5-$HT_{2A}$ receptors. It is also suspected that the agonism of the 5-$HT_{2A}$ receptors is responsible for some of the side effects attributed to the SSRIs, including sexual dysfunction.

Recently, a drug under development drew fresh attention to the joint modulation of the 5-$HT_{1A}$ and 5-$HT_{2A}$ serotonin receptors, when its dual mechanism of action triggered promising effects in the treatment of female sexual dysfunctions. Although the mechanism of action of this drug has not yet been fully explained, the participation of these two receptors in female sexual functioning had already been addressed by Meston et al (*Current Opinion in Urology* (2001) 11: 603-609), who mentioned that there is evidence that the activation of the 5-$HT_2$ receptors would hamper sexual functioning, while the stimulation of the 5-$HT_{1A}$ receptors would facilitate this, which might be the reason why the SSRIs produce side effects.

In view of the matters set forth above, the quest for drugs that could interact simultaneously with the 5-$HT_{1A}$ and 5-$HT_{2A}$ receptors may well offer better control or more effective treatment for several disorders, which could be accompanied by a briefer latency period for the appearance of the therapeutic effect and also a reduction, moderation or elimination of the side effects that are noted when the SSRIs are employed, being agents that, due to their mechanism of action, trigger and increase in the serotonin concentration that acts in a non-selective manner on all the serotonin receptors.

Several pharmacological properties are attributed to substances belonging to the quinazolinone class. More specifically, with regard to the alkyl-phenylpiperazine-4(3H)-quinazolinones, derivatives of this type were described in the state of the art presenting sedative, hypnotic, anti-hypertensive and anti-inflammatory properties.

U.S. Pat. No. 3,047,462 describes 4 (3H)-quinazolinones, in addition to other 4-quinazolines, which present anti-inflammatory properties.

U.S. Pat. No. 3,073,826 describes 3-pyrrolidylmethyl-4 (3H)-quinazolinones, which present anti-inflammatory properties.

U.S. Pat. Nos. 3,086,910, 3,448,109 and 3,928,354 describe substituted 4 (3H)-quinazolinones, 2-methyl and 3-aryl, which are endowed with hypnotic, muscle relaxant and anti-spasmodic activities. The substances described in these documents present ample structural similarity with methaqualone and its derivatives, which are hypnotic agents whose sale was suspended due to their high potential for developing dependency and abuse.

U.S. Pat. No. 3,231,572 describes substituted 4 (3H) quinazolinones, 2-methyl or phenyl and substituted 3-alkyl-piperazinyl-phenyl that are useful as anti-inflammatory agents or sedative agents. The tests conducted with the compounds described in this document demonstrated that these substances are endowed with hypotensive and anti-histaminic properties, not presenting any sedative properties (*Journal of Organic Chemistry* (1969), 12: 936-938, Shin Hayao et al). U.S. Pat. No. 3,984,555 describes substituted aryl-piperazinyl-alkyl-4(3H) quinazolone derivatives that have hypotensive, anti-histaminic and analgesic properties. Most of the compounds synthesized in this document are di-substituted 4 (3H)-quinazolinones 6,7-methoxy, bound in position 2 of the quinazolinones by an alkyl chain of one, two or three carbon atoms with the piperazine-phenyl portion substituted by 2, 3 or 4 methyl, methoxy, chlorine or fluor. The authors affirm that these compounds are endowed with properties that are particularly useful in the treatment of hypertension.

U.S. Pat. No. 4,841,051 describes substituted 4 (3H)-quinazolinones ethyl-piperazine-phenyl-2-ethoxy that have an activity blocking the $\alpha_1$ receptors, being useful in the treatment of hypertension.

Compounds belonging to the quinazolinedione class were described in U.S. Pat. Nos. 3,274,194, 3,726,979, 4,335,127, 4,578,465 and 5,264,438.

U.S. Pat. No. 3,274,194 describes substituted 2,4 (1H,3H)-quinazolinediones-3-derivatives, which are useful as anti-inflammatory and sedative agents. This document describes pelanserin, a hypotensive agent that was subsequently discovered to be an antagonist of the 5-HT$_2$ receptors without presenting affinity for the 5-HT$_{1A}$ receptors. The description that these compounds are serotonin antagonists is presented in U.S. Pat. No. 3,726,979.

U.S. Pat. No. 4,335,127 describes substituted 2,4-(1H,3H) quinazolinediones-3-alkyl-piperidine derivatives as compounds that are powerful serotonin antagonists. Among the compounds most studied described in this patent are ketanserin, altanserin and butanserin. All these compounds are endowed with high affinity for the 5-HT$_{2A}$ receptors, without presenting any affinity for the 5-HT$_{1A}$ receptors.

U.S. Pat. No. 4,578,465 describes substituted 2,4-(1H,3H) quinazolinediones-alkyl-methoxy-phenyl-piperazine compounds, with serotonin antagonist properties and able to block the alpha-adrenergic receptors.

U.S. Pat. No. 5,264,438 describes derivatives belonging to the 2,4 (1H,3H)-quinazolinedione family, which are endowed with serotonin antagonist properties, acting particularly as antagonists of the 5-HT$_2$ receptors, in addition to presenting antagonist properties together with the $\alpha_1$-adrenergic receptors and agonists together with the dopaminergic receptors.

Other compounds presenting serotonin activity and the receptors involved, without belonging to the quinazolinone or quinazolinedione classes, were described in U.S. Pat. No. 3,717,634, GB 2.023.594 and 4.203.98.

U.S. Pat. No. 3,717,634 describes N-heteroaryl-cyclic-piperazinyl-alkyl compounds derived from 8-azaspyro[4,5]decane-7,8-dione, which are endowed with activity together with the 5-HT$_{1A}$ receptors, with the main representative being buspirone, an agent with anxiolytic properties. This substance acts as a partial agonist on the 5-HT$_{1A}$ receptors, not presenting interaction or affinity for the 5-HT$_{2A}$ receptors.

GB Patent 2.023.594 describes substituted 4-(3-trifluoromethyl-thiophenyl)-piperazines-1-alkyl which may have substitutions binding to the alkyl group. The compounds described present activity with the central nervous system.

U.S. Pat. No. 4,203,986 describes substituted m-trifluoromethyl phenylpiperazines N-alkyl and/or cycloalkyl presenting activity with the central nervous system and the cardiovascular system, associated with sedative, tranquilizing and anti-tussive properties. Among the documents that describe compounds with selective affinity for the 5-HT$_{1A}$ and 5-HT$_{2A}$ receptors are U.S. Pat. Nos. 5,576,318, 6,586,435 and 6,281,218 that describe N-substituted benzimidazolones by substituted alkyl mono and di-phenylpiperazines, with these compounds presenting affinity for the 5-HT$_{1A}$ and 5-HT$_{2A}$ receptors, being useful for the treatment of central nervous system disorders, such as the treatment of depression, anxiety, neurodegenerative diseases and psychoses, for example, among others. The best compound known compound in this class of substances described in these documents is flibanserin, a drug whose clinical trials showed that it was not efficient for the treatment of depression and that is currently undergoing clinical trials for the treatment of hypoactive sexual desire disorder and other female sexual dysfunctions.

Kleven et al (*Journal of Pharmacology and Experimental Therapeutics* (1997), 282: 747-759) describe other substances presenting affinities for the 5-HT$_{1A}$ and 5-HT$_{2A/2C}$ receptors and that may be useful in the treatment of anxiety and depression disorders. These substances, initially proposed in U.S. Pat. Nos. 4,797,489, 5,166,157, 5,565,455, 4,604,397 and 4,721,787, are at various phases of studies for the treatment of disorders related to the modulation of these receptors.

Although there are theories defending the possible clinical advantages of developing drugs directed towards the 5-HT$_{1A}$ and 5-HT$_{2A}$ receptors, the substances developed so far and presenting this activity profile have not yet demonstrated the clinical efficacy required for their approval by the regulatory authorities, in addition to demonstrating effects fall well below the effects obtained with the SSRIs.

Surprisingly, the current inventors synthesized a particular family of compounds of the substituted 4 (3H)-quinazolinones-alkyl-piperazine-phenyl type, whose representatives present a high affinity for the 5-HT$_{1A}$ and 5-HT$_{2A}$ receptors and thus may be useful in the treatment or cure of several disorders associated with these receptors.

So far, the 4 (3H)-quinazolinones similar to those now described demonstrated that they are endowed with anti-hypertensive and/or anti-histaminic properties, with no circumstantial evidence indicating that they might be useful for the treatment of disorders attributed to modulations of the serotonin system, more specifically acting on the $5\text{-HT}_{1A}$ and $5\text{-HT}_{2A}$ receptors.

Studies conducted with the compounds addressed by this invention demonstrated that they gather together the structural characteristics that are appropriate for binding with the $5\text{-HT}_{1A}$ and $5\text{-HT}_{2A}$ receptors, with these properties related to the adequate size of the alkyl chain for linking the 4 (3H)-quinazolinone portion with the phenylpiperazine portion, associated with the need for the presence of steering groups that are appropriate and correctly oriented in the phenyl portion of the phenylpiperazine to promote anchoring of the appropriate confirmation of these compounds to these receptors.

Thus, this invention addresses substituted 4 (3H)-quinazolinones-alkyl-piperazine-phenyl compounds that have an affinity for the $5\text{-HT}_{1A}$ and $5\text{-HT}_{2A}$ serotonin receptors, with these compounds being useful in the treatment of persons affected by disorders associated with these receptors, such as depression, anxiety, phobias, addictions, aggressiveness, impulsiveness, panic, eating, sleep and psychotic disorders and obsessive-compulsive disorder in addition to being able to act on the heat regulation mechanism, presenting neuroprotective properties and also able to act on or assist with the treatment of female sexual dysfunctions, which encompass hypoative sexual desire disorder, sexual aversion disorder, female sexual excitation disorder, and the loss, inhibition or absence of sexual desire.

BRIEF DESCRIPTION OF THE FIGURE

FIG. 1 refers to a graph obtained from the responses to the in vivo efficacy test for the inventive compounds presented in Examples 1 and 2, and the comparative compound constituting the state of the art. The quantified values correspond to the number of observations conducted on the parameters: head twitches (HT), fore paw treading (FPT), flat body posture (FBP), hind-limb splay (HLS), lower lip retraction (LLR) and spontaneous tail flicks (STF).

DESCRIPTION OF THE INVENTION

This invention is related to the general formula compounds (I) shown below:

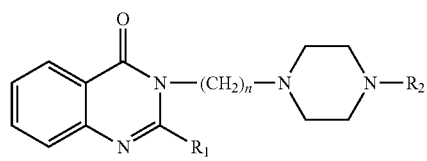

(I)

where, n=2;

$R_1$ is hydrogen or ethyl and $R_2$ is selected from the group consisting of 3-trifluormethylphenyl, 2-chlorophenyl, 2-methylphenyl, 2,3-dimethylphenyl, 2-cyanophenyl, 2-methoxyphenyl and 2-ethoxyphenyl, which are useful in the treatment of disorders associated with the $5\text{-HT}_{1A}$ and $5\text{-HT}_{2A}$ serotonin receptors.

The specific preferred compounds in the general formula (I) are:
3-(2-(4-(3-(trifluoromethyl)phenyl)piperazine-1-yl)ethyl) quinazoline-4(3H)-one;
3-(2-(4-o-tolylpiperazine-1-yl)ethyl)quinazoline-4(3H)-one;
3-(2-(4-(2,3-dimethylphenyl)piperazine-1-yl)ethyl)quinazoline-4(3H)-one;
3-(2-(4-(2-chlorophenyl)piperazine-1-yl)ethyl)quinazoline-4(3H)-one;
3-(2-(4-(2-cyanophenyl)piperazine-1-yl)ethyl)quinazoline-4(3H)-one;
3-(2-(4-(2-methoxyphenyl)piperazine-1-yl)ethyl)quinazoline-4(3H)-one;
2-ethyl-3-(2-(4-(2-(trifluoromethyl)phenyl)piperazine-1-yl) ethyl)quinazoline-4(3H)-one;
3-(2-(4-(2,3-dimethylphenyl)piperazine-1-yl)ethyl)-2-ethylquinazoline-4(3H)-one;
3-(2-(4-(2-chlorophenyl)piperazine-1-yl)ethyl)-2-ethylquinazoline-4(3H)-one;
2-ethyl-3-(2-(4-(2-methoxyphenyl)piperazine-1-yl)ethyl) quinazoline-4(3H)-one;
3-(2-(4-(2-ethoxyphenyl)piperazine-1-yl)ethyl)-2-ethylquinazoline-4(3H)-one.

The general formula compounds (I) above are basic in nature, being able to form salts for addition with various organic and inorganic acids. Thus, this invention also encompasses the appropriate pharmaceutical salts of the general formula compounds (I), which may be formed with non-toxic inorganic acids or organic acids.

The general formula compounds (I), or their appropriate pharmaceutical salts, may be administered alone or in the form of a pharmaceutical composition. Thus, this invention also has as an objective a pharmaceutical composition for treating disorders associated with the $5\text{-HT}_{1A}$ and $5\text{-HT}_{2A}$ receptors, encompassing at least one of the general formula compounds (I) in a therapeutically efficacious quantity, or its appropriate pharmaceutical salts, associated with at least one appropriate pharmaceutical excipient.

This invention is also related to the use of the general formula compounds (I) or their appropriate pharmaceutical salts for the treatment or the prevention of disorders associated with the $5\text{-HT}_{1A}$ and $5\text{-HT}_{2A}$ receptors, such as: depression, anxiety, phobias, panic, addictions, aggressiveness, impulsiveness, eating disorders, sleep disorders, obsessive-compulsive disorder, psychotic disorders, disorders involving the heat regulation mechanism, and as a neuroprotetor medication as well as for female sexual dysfunctions, which encompass hypoative sexual desire disorder, sexual aversion disorder, female sexual excitation disorder, and the loss, inhibition or absence of sexual desire.

Another objective of this invention is the use of the general formula compounds (I) or their appropriate pharmaceutical salts it may be used to prepare medication for the treatment and/or the prevention of disorders associated with the $5\text{-HT}_{1A}$ and $5\text{-HT}_{2A}$ receptors, such as: depression, anxiety, phobias, panic, addictions, aggressiveness, impulsiveness, eating disorders, sleep disorders, obsessive-compulsive disorder, psychotic disorders, disorders involving the heat regulation mechanism, and as a neuroprotetor medication as well as for female sexual dysfunctions, which encompass hypoative sexual desire disorder, sexual aversion disorder, female sexual excitation disorder, and the loss, inhibition or absence of sexual desire.

This invention also has as an objective a method for treating an individual mammal, including human beings, which consists of administering a therapeutically efficacious quantity of a compound of the formula (I), or its appropriate pharmaceutical salts, for the treatment of disorders selected from the group consisting of: depression, anxiety, phobias, panic, addictions, aggressiveness, impulsiveness, eating disorders, sleep disorders, obsessive-compulsive disorder, psychotic disorders, disorders involving the heat regulation mechanism, female sexual dysfunctions, which encompass hypoative sexual desire disorder, sexual aversion disorder, female sexual excitation disorder, and the loss, inhibition or absence of sexual desire, and also its use as a neuroprotector.

The general formula compounds (I) of this invention may be prepared through various routes using the usual synthesis methods. In this invention, these compounds were prepared through the stages presented in Diagram 1 below.

tion was submitted to reaction with monoethanolamine for the formation of the intermediate 2-ethyl-3-(hydroxymethyl) quinazoline-4(3H)-one. A reaction of this intermediate with thionyl chloride resulted in the chlorated derivative, which was subsequently condensed with the substituted piperazine phenyl, resulting in the desired compounds.

Although the general formula compounds (I) were prepared using the reaction stages described in Diagram 1, other synthetic approaches may be used to obtain them, without adversely affecting the outcome.

The synthetic route used proved to be quite practical for obtaining the compounds addressed by this invention, which may be easily isolated and purified.

DIAGRAM 1

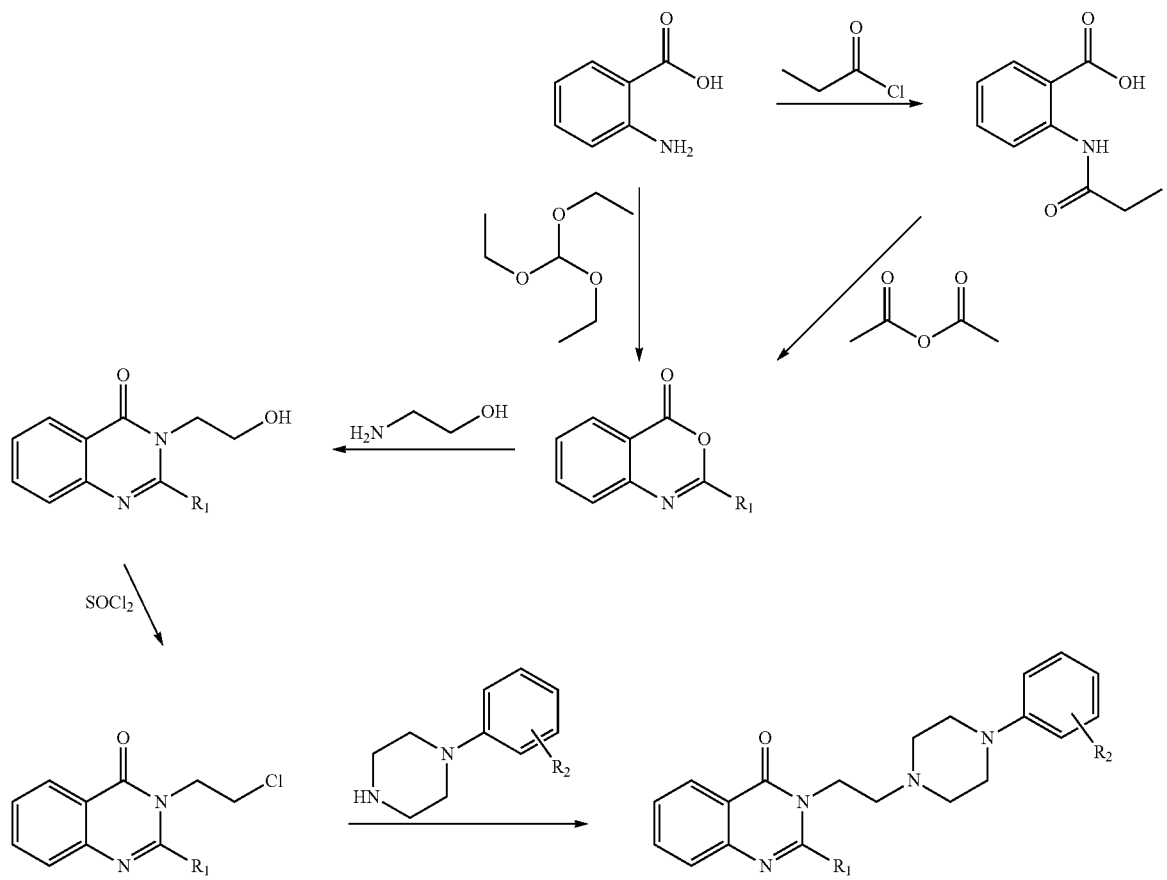

Pursuant to Diagram 1, the general formula compounds (I) where $R_1$ is substituted by hydrogen and $R_2$ is as described previously, were prepared from anthranilic acid, using ethyl orthoformate and monoethanolamine for the formation of the intermediate 3-(2-hydroxyethyl)quinazoline-4(3H)-one. The reaction of this intermediate with the thionyl chloride resulted in the formation of the chlorated derivative, which was subsequently condensed with the substituted piperazine phenyl resulting in the desired compounds.

The general formula compounds (I) where $R_1$ is substituted ethyl and $R_2$ is as described previously, were prepared that was submitted to reaction with propanoyl chloride with the anthranilic acid generating 2-propionamide benzoic acid. The reaction of this intermediate with the acetic anhydride resulted in the substituted benzoxazinone-2-ethyl. The reac- Examples of synthesizing the compounds are described in Examples 1 to 11.

The general formula compounds (I) of this invention are endowed with a basic nature and may form salts for addition with various organic and inorganic acids.

Examples of organic acids appropriate for use in the formation of the appropriate pharmaceutical salts of the general formula compounds (I) are: fumaric, acetic, propionic, benzoic, ascorbic, pamoic, succinic, oxalic, salicylic, maleic, tartaric, citric, lactic, malic, stearic, palmitic, benzenesulfonic, p-toluenesulfonic, methanesulfonic, ethanesulfonic, aspartic, mandeic, cinnamic, glycolic, gluconic, glutamic and p-aminobenzoic, among others.

Examples of inorganic acids appropriate for use in the formation of the appropriate pharmaceutical salts of the general formula compounds (I) are: hydrochloric, hydrobromic, sulfuric, phosphoric and nitric, among others.

The pharmaceutical salts of the general formula compounds (I) may be prepared through the usual procedures described in the state of the art, using the conditions and solvents appropriate for their formations. The acid salts for adding to the compound addressed by this invention may be easily prepared through treating the base compound with a molar quantity equivalent to or in excess of the selected acid, using organic solvents, blends of organic solvents, and blends of organic solvents and water.

The compounds addressed by this invention and/or its appropriate pharmaceutical salts may be administered alone or in the form of a pharmaceutical composition. When administered in the form of a pharmaceutical composition, the compounds addressed by this invention or the appropriate pharmaceutical salts thereof will be associated with at least one conventional or appropriate pharmaceutical excipient.

Pursuant to this invention, a conventional or appropriate pharmaceutical excipient is deemed to be any substance other than the active pharmaceutical ingredient, that has been appropriately assessed in terms of its safety and has been intentionally included in a pharmaceutical dosing form.

The selection of excipients to be used or preparing pharmaceutical compositions is generally undertaken by taking into consideration the type of administration pathway, the physical and chemical compatibility of the excipient with the active ingredient, the manner of preparing the pharmaceutical presentation and the effects on its efficacy. These excipients are widely known in the state of the art and are described in the literature (*Handbook of Pharmaceutical Manufacturing Formulations—Vol.* 1 a 6-2004—Sarfaraz K. Niazi—CRC Press and Remington's Pharmaceutical Sciences, Mack Publishing), widely used by technical experts in the matter.

Pharmaceutical excipients usually classified or sub-classified on the basis of the function that they perform in the pharmaceutical compositions and/or in their manufacturing technique. They may be called diluting agents, binding agents, breakdown or anti-clumping agents, lubricants, suspension agents, thickening agents, solvents, surfactants, slip agents, anti-clumping or flow agents, coating agents, plastifying agents, sweeteners, isotonicity agents, colorants, conservants, antioxidants, pH control or modification agents, complexing agents used to mask flavor, improve solubility, promote formulation stability, and modulate bioavailability, in addition to chelating, aromatizing and flavorizing agents.

Diluting agents are pharmaceutical excipients included in solid dosage forms, such as tablets, capsules, pills, pellets, powders and granules, in order to increase the volume or the weight of the type of dosage. They also may be used in liquid and semi-solid pharmaceutical forms for the same purpose. Examples of diluting agents appropriate for the preparation of pharmaceutical compositions of this invention include but are not limited to: calcium carbonate, calcium phosphates, calcium sulfate, microcrystal cellulose, powdered cellulose, dextrins, dextrose, fructose, kaolin, anhydrous and/or monohydrated lactose, maltose, sorbitol, assorted starches (maize, wheat, potato, tapioca), pre-gelatinized starch, saccharose and sugar.

Binding agents are pharmaceutical excipients that are included in the formulations in order to ensure easier clumping of powders into granules during the blending (or granulation) stage, using water as a granulation fluid, or hydroalcohol mixtures or other solvents. Binding agents may also be used in dry blending processes where no fluids are required. Examples of binding agents appropriate for the preparation of the pharmaceutical composition of this invention include but are not limited to: acacia gum, alginic acid, ammonium methacrylate copolymer, carbomer copolymer or homopolymer or interpolymer, starches (maize, wheat, potato, tapioca), microcrystal cellulose, methyl cellulose, ethyl cellulose, hydroxypropylmethyl cellulose, dextrin, maltodextrin, maltose, saccharose, gelatin, glucose, guar gum and povidone.

Breakdown or anti-clumping agents are pharmaceutical excipients that can speed up the breakdown or dissolution of the formulation when in contact with biological fluids. Examples of breakdown or anti-clumping agents appropriate for the preparation of the pharmaceutical composition of this invention include but are not limited to: alginic acid, starches, sodium alginate, sodium croscaramelose, sodium glycolate, sodium carboxymethyl cellulose, microcrystal cellulose and crospovidone.

Lubricants are excipients that reduce friction among the particles in the formulations and also lessen the friction between the particles and the walls of the equipment used to prepare them. Examples of lubricants appropriate for the preparation of the pharmaceutical composition of this invention include but are not limited to: calcium stearate, magnesium stearate, zinc stearate, mineral oil, polyethylene glycol, sodium lauryl sulfate, sodium stearyl fumarate, starch, stearic acid, talc and type I hydrogenated vegetable oil.

Suspension agents and thickening agents are excipients used in formulations to ensure the stability of dispersed systems (for example, suspensions and emulsions), in order to reduce particle sedimentation speed or to lessen the fluidity of liquid formulations. Examples of appropriate suspension agents and thickening agents for preparing the pharmaceutical composition of this invention include but are not limited to: acacia gum, agar, alginic acid, aluminum monostearate, bentonite, carbomer, copolymer carbomer, homopolymer carbomer, interpolymer carbomer, calcium or sodium carboxymethyl cellulose, carrageenan, microcrystal cellulose, dextrin, guar gum, gellan gum, hydroxyethyl cellulose, hydroxypropylcellulose, methyl cellulose, aluminum magnesium silicate, pectin, polyethylene oxide, polyvinyl alcohol, povidone, propylene glycol alginate, sodium alginate, silicon dioxide, colloidal silicon dioxide, starches (maize wheat, potato, tapioca), tragacanth gum and xanthan gum.

Solvents are excipients employed to dissolve other substances when preparing liquid, semi-solid and solid compositions, used for the latter in order to ensure easier blending and/or to provide a blend with a homogeneous concentration of the active pharmaceutical ingredient or some other excipient. Examples of solvents appropriate for the preparation of the pharmaceutical composition of this invention include but are not limited to: water, ethanol, isopropanol, plant oils (maize, cotton, sesame, soy), mineral oil, glycerin, sorbitol and oleic acid.

Surfactants are also known as surface tension modulation agents, and are excipients with assorted functions, used as emulsifiers, humectants and/or solubilization agents. Examples of surfactants appropriate for the preparation of the pharmaceutical composition of this invention include but are not limited to: benzalkonium chloride, benzethonium chloride, cetylpyridinium chloride, nonoxynol 9, octoxynol 9, polyoxyl 50 stearate, polyoxyl 10 oleyl ether, polyoxyl 20 cetostearyl ether, polyoxalate 35 ricin oil, hydrogenated polyoxalate 40 ricin oil, polyoxyl 40 stearate, polyoxyl lauryl ether, polyoxyl stearyl ether, polysorbate 20, polysorbate 40, polysorbate 60, polysorbate 80, sodium cetoestearyl sulfate, sodium lauryl sulfate, sorbitan monolaurate, sorbitan monoleate, sorbitan monoplamitate, sorbitan sesquioleate, sorbitan trioleate, cetyl alcohol, oleyl alcohol, poloxamer, propylene glycol monostearate, carbomer copolymer or interpolymer, cholesterol, monoethanolamine, diethanolamine, triethanolamine, diethylene glycol stearates, sodium docusate, ethylene glycol stearates, glyceryl distearates, glyceryl monolinoleate, glyceryl monooleate, glyceryl monostearate, lanolin alcohols, lecithin, mono and diglycerides, sodium stearate, stearic acid and emulsifying wax.

Flow agents, anti-clumping or slip agents are excipients used in formulations to promote flows and reduce clumping in solids conduction funnels during powder flows and processing. Examples of flow agents, anti-clumping or slip agents appropriate for the preparation of the pharmaceutical composition of this invention include but are not limited to: calcium silicate, magnesium silicate, colloidal silicon dioxide and talc.

Coating agents are excipients that may be used with various functions, including masking unpleasant flavors or odors, controlling drug release speed, enhancing appearance, easier swallowing and controlling the release of the drug in the digestive tract (for example enteric coating). Examples of coating agents appropriate for the preparation of the pharmaceutical composition of this invention include but are not limited to: ammonium methacrylate copolymer, sodium carboxymethyl cellulose, cellulose acetate phthalate, cellulose acetate, copovidone, ethyl cellulose and its aqueous dispersions, gelatin, pharmaceutical varnishes, hydroxypropyl cellulose, hydroxypropylmethyl cellulose, hydroxypropyl methylcellulose acetate succinate, hydroxypropylmethyl cellulose phthalate, maltodextrin, methacrylic acid copolymer and its dispersions, methyl cellulose, polyethylene glycol, polyvinyl acetate phthalate, shellac, modified pre-gelatinized starch, saccharose, titanium dioxide, carnauba wax and microcrystal wax.

Plastifying agents are excipients added to other agents in order to endow them with greater plasticity and resilience (elasticity). They are important components for conferring the physical properties required by polymer systems. Examples of plastifying agents appropriate for the preparation of the pharmaceutical composition of this invention include but are not limited to: acetyl tributyl citrate, acetyl triethyl citrate, ricin oil, diacetylated monoglycerides, dibutyl sebacate, sorbitol, dextrin, diethyl phthalate, glycerin, polyethylene glycol, polyethylene glycol monomethyl ether, propylene glycol, benzyl benzoate, triacetin, tributyl citrate, triethyl citrate and chlorobutanol.

For parenteral administration, it is normal to use isotonic solutions, meaning solutions with osmotic pressure similar to the tissues with which they come into contact, in order to avoid hemolyses, reducing pain and the discomfort of administration. Examples of isotonicity agents frequently used to ensure the isotonicity of the pharmaceutical composition of this invention include but are not limited to: dextrose, glycerin, manitol, sodium chloride, and potassium chloride.

Sweeteners are agents used to mask unpleasant flavors and sweeten oral formulations. Examples of sweeteners appropriate for the preparation of the pharmaceutical composition of this invention include but are not limited to: acesulfame potassium, aspartame, acesulfame aspartame salt, dextrates, dextrose, fructose, galactose, maltitol, maltose, manitol, saccharine, calcium saccharine, sodium saccharine, sorbitol, sucralose, saccharose, sugar and tagatose.

The scope of the composition addressed by this invention also encompasses pharmaceutical colorants that are included in the dosing forms, in order to endow each medication with a distinct appearance, ensuring that it is easy to distinguish a specific formulation among formulations with similar physical aspects. Examples of pharmaceutical colorants appropriate for use in the composition of this invention include: red ferric oxide, yellow ferric oxide, ferric oxide blends, caramel, titanium dioxide, FD&C colorants and D&C colorants.

Depending on the administration pathway and the physical and chemical properties inherent to the compounds addressed by this invention, substances may be added to the pharmaceutical composition prepared with these compounds that can stabilize, preserve, prevent and/or avoid the premature degradation of its ingredients. These additional excipients may act as antioxidants, conservants, pH regulators or modifiers. Examples of excipients used with these properties that are appropriate for the preparation of the pharmaceutical composition addressed by this invention include but are not limited to: ascorbic acid, sorbic acid, sodium meta bisulfite, alpha-tocopherol, methylparaben, propylparaben, butylparaben, sodium sulfite, butylated hydroxytoluene (BHT), butylated hydroxyanisole (BHA), phenol, benzyl alcohol, benzalkonium chloride, benzethonium chloride, cetylpyridinium chloride, benzoic acid, sodium benzoate, sodium propionate, boric acid and the pH control agents, the latter encompassing organic and inorganic acids, basis and buffers and normally used in pharmaceutical compositions.

The pharmaceutical composition encompassing the compounds addressed by this invention may also contain substances or be prepared with: (a) complexing agents to mask flavor, improve solubility, promote the solubility of the formulation and/or modulate bioavailability, and (b) aromatizing and flavorizing agents used to correct or mask unpleasant odors and flavors, or to confer pleasant odors and flavors. Several substances and preparations are available on the market for such applications, with their use being limited to approved agents, or those that have been duly certified, which are compatible with the ingredients in the composition.

For therapeutic use and administration, the compounds addressed by this invention or its appropriate pharmaceutical salts may be formulated as set forth in compositions appropriate for oral, parenteral, nasal, rectal, transmucosal and transdermal administration, using conventional techniques and appropriate excipients. Thus, the compounds addressed by this invention may be prepared as tablets, pills, capsules, dragées, granules, powders, pellets, aerosols, elixirs, solutions, lyophilizates, suspensions, syrups, suppositories and patches, among other known forms that are appropriate for the administration pathways.

The therapeutic dose to be used of the compounds addressed by this invention must be planned and calculated in compliance with the selected administration pathway, the weight and condition of the patient and the severity of the disorder being treated. In general, the compounds addressed by this invention are administered at therapeutically efficacious doses that vary from about 0.1 mg to about 1,000 mg per day, preferably 0.5 mg to 500 mg per day, but also preferably 1 mg to 250 mg per day, administered in a single or fractioned dose.

The determination of the activity of the synthesized compounds was conducted through assays assessing affinity with the $5\text{-HT}_{1A}$ and $5\text{-HT}_{2A}$ serotonin receptors. The assays used are based on the binding ratings of the substances being tested at different concentrations, compared to the affinity in the single concentration of the radioligands (markers) that have a specific affinity for these receptors.

These assays, known as binding assays and also known as inhibition experiments, are able to determine the affinity of a substance through the receptor, provided that this substance is soluble under the assay conditions.

In an inhibition experiment, the quantity of an inhibitor substance (non radioactive—sample or compound being tested) included in the incubation is the only variable, meaning that it is possible to determine for each test drug concentration, the binding inhibition percentage of the radioligand.

$CI_{50}$ is a value defined as the concentration of an unbranded substance (test sample) required to inhibit the specific binding of the radioligand in 50% of the receptors.

The affinity assays with the $5\text{-}HT_{1A}$ and $5\text{-}HT_{2A}$ receptors of the compounds addressed by this invention were conducted by the Biochemical and Molecular Pharmacology Laboratory at the Biomedical Science Institute in Rio de Janeiro Federal University (UFRJ), using its own protocols.

For the efficacy assay, the compounds addressed by this invention were submitted to the modified Irwin assay. The assays were conducted by Porsolt, using a specific protocol for evaluation.

Non-exhaustive examples are presented below that illustrate the preparation of compounds addressed by this invention, the assays to which they were submitted, and the results with comments on the affinity tests conducted on the $5\text{-}HT_{1A}$ and $5\text{-}HT_{2A}$ receptors and the efficacy test to which the compounds were submitted, demonstrating the relevance and usefulness of this invention.

EXAMPLES

Example 1

Preparation of 3-(2-(4-(3-(trifluoromethyl)phenyl) piperazine-1-yl)ethyl)quinazoline-4(3H)-one 1a. 3-(2-hydroxyethyl)quinazoline-4(3H)-one A mixture of 2-aminobenzoic acid (2 g, 14.58 mmol), triethyl o-formate (6.07 mL, 36.4 mmol) and ethanolamine (0.94 ml, 15.54 mmol) was maintained in reflux for three hours. The reaction medium was cooled to room temperature, adding 50 mL of water. The resulting suspension was kept in agitation at 15° C. for 4 hours and was then vacuum filtered. The raw product obtained was recrystalized ethanol yielding 3-(2-hydroxyethyl)quinazoline-4(3H)-one (2.5 g, yield=90%) as a white solid.

1b. 3-(2-chloroethyl)quinazoline-4(3H)-one

This thionyl chloride (1,095 mL, 15 mmol) was added to 3-(2-hydroxyethyl)quinazoline-4(3H)-one (2.0 g, 10.52 mmol) in a reactor, forming a white suspension that heated spontaneously to 85° C. The reaction medium was kept at this temperature under agitation for thirty minutes, after which it was left to cool to about 40° C. Next, 50 mL of water was added, forming a pinkish suspension, which was kept under agitation for two hours. The product was then vacuum filtered and washed with three portions of 10 mL of an ethanol/water mixture (50% v/v), yielding 3-(2-chloroethyl)quinazoline-4 (3H)-one as a pale white solid (1.8 g, 8.63 mmol, yield=82%).

1c. 3-(2-(4-(3-(trifluoromethyl)phenyl)piperazine-1-yl)ethyl)quinazoline-4(3H)-one The following were added to a 250 mL reactor: 3-(2-chloroethyl) quinazoline-4(3H)-one (1 g, 4.79 mmol), 1-(3-(trifluoromethyl)phenyl)piperazine (1,103 g, 4.79 mmol), sodium carbonate (0.762 g, 7.19 mmol), sodium iodide (0.072 g, 0.479 mmol), ethanol (50 ml) and toluene (150 ml). The reaction medium was kept under agitation and reflux for a period of twenty hours, during which 150 ml of the solvent were removed slowly with the assistance of a Dean-Stark. To the resulting mixture, 100 mL of an aqueous solution of acetic acid were added at 10% and 150 mL of ethyl acetate. The mixture was agitated, the organic phase separated, washed with 2 portions of 50 mL of a 5% sodium bicarbonate solution, dry with $MgSO_4$, filtered and evaporated to dryness, yielding the raw product as a slightly yellowish oil. This oil was dissolved in isopropanol, adding 2 mL of concentrated HCl under agitation to the resulting solution. This agitation was maintained for two hours in order to complete the precipitation of the hydrochloride. The resulting solid was filtered and vacuum dried, yielding 1.45 g of 3-(2-(4-(3-(trifluoromethyl)phenyl)piperazine-1-yl)ethyl)quinazoline-4 (3H)-one hydrochloride (3.3 mmol, yield=69%).

Then 3-(2-(4-(3-(trifluoromethyl)phenyl)piperazine-1-yl) ethyl)quinazoline-4(3H)-one in its base form was obtained from the raw product resulting from the treatment of the reaction medium, using the following procedure:

5.0 g of raw 3-(2-(4-(3-(trifluoromethyl)phenyl)piperazine-1-yl)ethyl)quinazoline-4(3H)-one isolated through the treatment of the reaction medium was dissolved in 30 mL of isopropanol at 60° C. with agitation. The resulting solution was left to rest at a temperature of about 5° C. for a period of 12 hours to promote precipitation. The resulting solid was vacuum filtered, washed with two portions of 10 mL of isopropanol at 0° C. and dried, yielding the titered compound as white crystals (4.2 g; yield: 84%).

RMN $^1$H (DMSO-$d_6$, 300 MHz): □3.25-3.72 (4H, m, $(CH_2)_2$), 3.25-3.98 (4H, m, $(CH_2)_2$), 3.61 (2H, br s, $CH_2$), 4.50 (2H, m, $CH_2$), 7.1 (1H, dd, J=1.9 and 8 Hz), 7.3 (2H, m, $(CH)_2$), 7.5 (1H, m, (CH)), 7.55 (1H, m, (CH)), 7.7 (1H, dd, J=1.9 and 8.0 Hz, CH), 7.80 (1H, m, CH), 8.20 (1H, dd, J=1.9 and 8.0 Hz, CH), 8.50 (1H, s, CH).

RMN $^{13}$C (DMSO-$d_6$, 300 MHz): □40.3 (1C, $CH_2$), 44.7 (2C, $(CH_2)_2$), 50.7 (2C, $(CH_2)_2$), 53.8 (C1, $CH_2$), 111.6 (1C, CH), 112.2 (1C, CH), 119.2 (1C, CH), 120.8 (1C, qC), 122.4 (1C, $CF_3$), 126.0 (1C, CH), 126.1 (2C, CH), 130.0 (1C, CH), 130.2 (1C, qC), 134.0 (1C, CH), 147.0 (1C, qC), 147.1 (1C, CH), 149.8 (1C, qC),160.0 (1C, C=O).

EI-MS (70 ev): 402 [M]+, 243, 200, 172, 145, 102, 70

Example 2

Preparation of 3-(2-(4-o-tolylpiperazine-1-yl)ethyl) quinazoline-4(3H)-one

This compound was prepared in compliance with the procedure described in 1c, using 1-o-tolylpiperazine instead of 1-(3-(trifluoromethyl)phenyl)piperazine.

RMN $^1$H (DMSO-$d_6$, 300 MHz): □2.27 (3H, s, $CH_3$), 3.34 (2H, br s, $CH_2$), 3.05-3.25 (4H, m, $(CH_2)_2$), 3.05-3.72 (4H, m, $(CH_2)_2$), 4.47 (2H, t, J=6.0 Hz, $CH_2$), 7.01-7.20 (4H, m, $(CH)_4$), 7.58 (1H, dd, J=1.11 and 8.07 Hz, CH), 7.73 (1H, d, J=7.68 Hz, CH), 7.89 (1H, dd, J=1.5 and 7.17 Hz, CH), 8.20 (1H, dd, J=1.23 and 8.01 Hz, CH), 8.48 (1H, s, CH).

RMN $^{13}$C (DMSO-$d_6$, 300 MHz): □17.4 (1C, $CH_3$), 40.0 (1C, $CH_2$), 48.1 (2C, $(CH_2)_2$), 51.9 (2C, $(CH_2)_2$), 54.0 (C1, $CH_2$), 118.9 (1C, CH), 121.5 (1C, qC), 123.7 (1C, CH), 124.0 (1C, CH), 126.0 (1C, CH), 126.6 (1C, CH), 127.1 (1C, CH), 130.9 (1C, CH), 132.0 (1C, qC), 134.5 (1C, CH), 147.6 (1C, CH), 147.8 (1C, qC), 149.5 (1C, qC), 160.7 (1C, C=O).

EI-MS (70 ev): 348 [M]$^+$, 215, 189, 146, 118, 92, 70

Example 3

Preparation of 3-(2-(4-(2,3-dimethylphenyl)piperazine-1-yl)ethyl)quinazoline-4(3H)-one This compound was prepared in compliance with the procedure described in 1c, using 1-(2,3-dimethylphenyl)piperazine instead of 1-(3-(trifluoromethyl)phenyl)piperazine.

RMN $^1$H (DMSO-d$_6$, 300 MHz): ☐2.17 (3H, s, CH$_3$), 2.22 (3H, s, CH$_3$), 3.34 (2H, br s, CH$_2$), 3.05-3.64 (4H, m, (CH$_2$)$_2$), 3.05-3.72 (4H, m, (CH$_2$)$_2$), 4.68 (2H, t, J=6.0 Hz, CH$_2$), 6.91 (2H, m, (CH)$_2$), 7.59 (1H, m, CH), 7.73 (2H, m, (CH)$_2$), 7.85 (1H, m, CH), 8.20 (1H, m, CH), 8.48 (1H, s, CH).

RMN $^{13}$C (DMSO-d$_6$, 300 MHz): ☐14.7 (1C, CH$_3$), 21.3 (1C, CH$_3$), 40.0 (1C, CH$_2$), 49.7 (2C, (CH$_2$)$_2$), 53.1 (2C, (CH$_2$)$_2$), 55.2 (1C, CH$_2$), 117.8 (1C, CH), 122.7 (1C, qC), 126.8 (1C, CH), 127.0 (1C, CH), 127.2 (1C, CH), 128.4 (1C, CH), 131.8 (1C, qC), 135.7 (1C, CH), 138.7 (1C, qC), 148.8 (1C, qC), 149.0 (1C, CH), 150.8 (1C, qC), 162.0 (1C, C=O).

El-MS (70 ev): 362 [M]$^+$, 217, 173, 147, 120

Example 4

Preparation of 3-(2-(4-(2-chlorophenyl)piperazine-1-yl)ethyl)quinazoline-4(3H)-one This compound was prepared in compliance with the procedure described in 1c, using 1-(2-chlorophenyl)piperazine instead of 1-(3-(trifluoromethyl)phenyl)piperazine.

RMN $^1$H (DMSO-d$_6$, 300 MHz): ☐3.18-3.35 (4H, m, (CH$_2$)$_2$), 3.18-3.73 (4H, m, (CH$_2$)$_2$), 3.63 (2H, br s, CH$_2$), 4.49 (1H, t, J=6.0 Hz, CH$_2$), 7.11 (1H, t, J=7.5 Hz, CH), 7.23 (1H, d, J=7.62 Hz, CH), 7.34 (1H, t, J=7.29 Hz, CH), 7.46 (1H, d, J=8.3 Hz, CH), 7.58 (1H, m, CH), 7.72 (1H, d, J=8.07 Hz, CH), 7.89 (1H, t, J=7.29 Hz, CH), 8.20 (1H, d, J=7.71 Hz, CH), 8.48 (1H, s, CH).

RMN $^{13}$C (DMSO-d$_6$, 300 MHz): ☐40.0 (1C, CH$_2$), 47.5 (2C, (CH$_2$)$_2$), 51.6 (2C, (CH$_2$)$_2$), 53.9 (1C, CH$_2$), 121.0 (1C, qC), 121.5 (1C, qC), 124.8 (1C, CH), 126.0 (1C, CH), 127.1 (1C, CH),127.2 (1H, CH), 127.5 (1C, CH), 128.2 (1C, CH), 130.4 (1C, CH), 134.4 (1C, CH), 147.7 (1C, CH), 147.8 (2C, qC), 160.6 (1C, C=O).

El-MS (70 ev): 368 [M]$^+$, 223, 209, 166, 159, 138, 111, 70

Example 5

Preparation of 3-(2-(4-(2-cyanophenyl)piperazine-1-yl)ethyl)quinazoline-4(3H)-one This compound was prepared in compliance with the procedure described in 1c, using 2-(piperazine-1-yl)benzonitryl instead of 1-(3-(trifluoromethyl)phenyl)piperazine.

RMN $^1$H (DMSO-d$_6$, 300 MHz): ☐3.65 (2H, br s, CH$_2$), 3.36-3.65 (4H, m, (CH$_2$)$_2$), 3.36-3.80 (4H, m, (CH$_2$)$_2$), 4.52 (2H, t, J=6.0 Hz, CH$_2$), 7.21 (1H, m, CH), 7.28 (1H, m, CH), 7.56 (1H, m, CH), 7.65 (1H, m, CH), 7.72 (1H, t, J=7.74 Hz, CH), 7.7 (1H, d, J=1.53 and 7.69, CH), 7.87 (1H, td, J=1.53 and 7.23 Hz, CH), 8.20 (1H, dd, J=1.2 and 7.98 Hz, CH), 8.58 (1H, s, CH).

RMN $^{13}$C (DMSO-d$_6$, 300 MHz): ☐40.8 (1C, CH$_2$), 44.0 (2C, (CH$_2$)$_2$), 50.5 (2C, (CH$_2$)$_2$), 53.4 (1C, CH$_2$), 105.1 (1C, qC), 117.8 (1C, CH), 119.4 (1C, CH), 121.4 (1C, qC), 123.0 (1C, C≡N), 126.0 (1C, CH), 126.8 (1C, CH), 127.2 (1C, CH), 134.2 (1C, CH), 134.4 (1C, CH), 134.5 (1C, CH), 147.3 (1C, qC), 147.8 (1C, CH), 153.3 (1C, qC), 160.5 (1C, C=O).

El-MS (70 ev): 359 [M]+, 217, 200, 159, 157, 129, 108, 70

Example 6

Preparation of 3-(2-(4-(2-methoxyphenyl)piperazine-1-yl)ethyl)quinazoline-4(3H)-one This compound was prepared in compliance with the procedure described in 1c, using 1-(2-methoxyphenyl)piperazine instead of 1-(3-(trifluoromethyl)phenyl)piperazine.

RMN $^1$H (DMSO-d$_6$, 300 MHz): ☐☐3.50 (2H, br s, CH$_2$), 3.80 (3H, s, OCH$_3$), 3.26-3.53 (4H, m, (CH$_2$)$_2$), 3.26-3.68 (4H, m, (CH$_2$)$_2$), 4.49 (1H, t, J=6.0 Hz, CH$_2$), 6.92 (1H, m, CH), 6.96 (1H, m, CH), 7.00 (1H, d, J=8.0 Hz, CH), 7.04 (1H, d, J=8.0 Hz, CH), 7.58 (1H, dd, J=1.53 and 8.13 Hz, CH), 7.72 (1H, d, J=8.0 Hz, CH), 7.86 (1H, td, J=1.53 and 8.13 Hz, CH), 8.18 (1H, dd, J=1.1 and 7.98 Hz, CH), 8.50 (1H, s, CH).

RMN $^{13}$C (DMSO-d$_6$, 300 MHz): ☐☐40.0 (1C, CH$_2$), 46.7 (2C, (CH$_2$)$_2$), 51.5 (2C, (CH$_2$)$_2$), 53.8 (1C, CH$_2$), 55.3 (1C, OCH$_3$), 111.9 (1C, CH$_2$), 118.9 (1C, CH), 120.8 (1C, qC), 121.5 (C1, CH), 123.4 (C1, CH), 126.0 (C1, CH), 127.0 (C1, CH), 127.1 (C1, CH), 134.4 (C1, CH), 139.3 (1C, qC), 147.6 (1C, CH), 147.8 (1C, qC), 151.8 (1C, qC), 160.6 (1C, C=O).

El-MS (70 ev): 364 [M]$^+$, 217, 205, 191, 162, 143, 120, 93, 70

Example 7

Preparation of 2-ethyl-3-(2-(4-(3-(trifluoromethyl)phenyl)piperazine-1-yl)ethyl)quinazoline-4(3H)-one 7a. 2-ethyl-4H-3,1-benzoxazin-4-one Propanoyl chloride (6.2 g, 67 mmol) was added to a solution of anthranilic acid (1 g, 7.3 mmol) in dichloromethane (20 mL). The reaction medium was kept under reflux and agitation, with the end of the reaction being monitored by CG/MS. After the end of the reaction, a hydrochloric acid solution was added (20 mL, 1M), and the resulting mixture was extracted with ethyl acetate (100 mL), the extract was dried with magnesium sulfate and the solvent was evaporated. Acetic anhydride (15 mL) was added to the residue and the reaction medium was taken to reflux and accompanied through CG/MS in order to monitor cyclization. After the end of the reaction, the reaction medium spin dried at a temperature of 65° C. using portions of toluene to facilitate the elimination of the anhydride. 1.0 g of the raw product 2-ethyl-4H-3,1-benzoxazin-4-one was obtained, which was used directly in the stage subsequent to reaction.

7b. 2-ethyl-3-(2-hydroxyethyl)quinazoline-4(3H)-one 1 g of 2-ethyl-4H-3,1-benzoxazin-4-one was added to 10 mL of monoethanolamine and the mixture was heated to 100° C. for 40 minutes. The heating element was then removed and the reaction medium was kept under agitation for about eight hours (end of the reaction). 100 mL were added to the reaction medium and the mixture was extracted with three portions of 25 mL of ethyl acetate. The organic phase was separated, and dried with magnesium sulfate and spin dried, yielding the 2-ethyl-3-(2-hydroxyethyl)quinazoline-4(3H)-one compound as a yellowish oil, which solidified when left to rest at room temperature, which was used in the next stage, with no purification.

Yield: 0.95 g (76%)

7c. 3-(2-chloroethyl)-2-ethylquinazoline-4(3H)-one 2-ethyl-3-(2-hydroxyethyl)quinazoline-4(3H)-one (5.00 g; 22.91 mmol) and thionyl chloride (1.672 mL, 22.91 mmol) were added to a 150 mL reactor, together with 60 mL of chloroform. The reaction medium was heated to reflux and for completing the reaction, which was accompanied through CG/MS. After the end of the reaction, 100 mL of hexane were added and the solution was agitated at room temperature in order to precipitate the product. The resulting suspension was vacuum filtered, washed with two portions of hexane and dried, yielding 3-(2-chloroethyl)-2-ethylquinazoline-4(3H)-one as a white solid (1.78 g; 7.52 mmol; yield: 32.8%).

7d. 2-ethyl-3-(2-(4-(3-(trifluoromethyl)phenyl)piperazine-1-yl)ethyl)quinazoline-4(3H)-one 3-(2-chloroethyl)-2-ethylquinazoline-4(3H)-one (1.5 g; 6.34 mmol), 1-(3-(trifluoromethyl)phenyl)piperazine (1.459 g; 6.34 mmol), sodium carbonate (0.672 g; 6.34 mmol), sodium iodide (0.95 g; 6.34 mmol), ethanol (100 mL) and toluene (200 mL) were added to a 100 mL reactor. The reaction medium was heated to reflux and kept under agitation for a period of 24 hours, during which 250 mL of solvent were slowly removed with assistance from a Dean Stark. The reaction was monitored through CG/MS until completion. After the end of the reaction, ethyl acetate (250 mL) was added, together with an aqueous solution of acetic acid (100 mL; 10%). The mixture was maintained under agitation for a period of 30 minutes. The organic phase was separated, washed with two portions of 50 mL of $NaHCO_3$ at 5%, dried with $MgSO_4$ and evaporated at reduced pressure, yielding a pale yellow colored oil (2.7 g of raw 2-ethyl-3-(2-(4-(3-(trifluoromethyl)phenyl)piperazine-1-yl)ethyl)quinazoline-4(3H)-one). This oil was dissolved in isopropanol, adding 2.0 mL of concentrated HCl to the resulting solution. The solution was kept under agitation at room temperature, until completing precipitation of the solids. The solids were vacuum filtered, washed with two portions of 5 mL of isopropanol and dried, yielding 2-ethyl-3-(2-(4-(3-(trifluoromethyl)phenyl)piperazine-1-yl)ethyl)quinazoline-4(3H)-one hydrochloride as a pale white solid (2.36 g, 5.48 mmol, yield: 87%).

The 2-ethyl-3-(2-(4-(3-(trifluoromethyl)phenyl)piperazine-1-yl)ethyl)quinazoline-4(3H)-one was prepared through dissolving the isolated raw product in oil, as described above, through dissolving it in boiling isopropanol, followed by cooling to room temperature, then leaving it at 5° C. for a period of 12 hours, during which the product precipitated.

RMN $^1$H (DMSO-$d_6$, 300 MHz): □□1.34 (3H, t, J=6.96 Hz, $CH_3$), 3.03 (2H, dd, J=6.75 and 13.86 Hz, $CH_2$), 3.29-3.75 (4H, m, $(CH_2)_2$), 3.29-4.00 (4H, m, $(CH_2)_2$), 3.48 (2H, br s, $CH_2$), 4.5 (2H, m, $CH_2$), 7.17 (1H, d, J=7.35 Hz, CH), 7.3 (2H, d, J=9.48 Hz, $(CH)_2$), 7.5 (2H, m, CH), 7.6 (1H, m, CH), 7.82 (1H, m, CH), 8.13 (1H, d, J=7.74 Hz, CH).

RMN $^{13}$C (DMSO-$d_6$, 300 MHz): □10.8 (1C, $CH_3$), 27.2 (1C, $CH_2$), 40.0 (1C, $CH_2$), 44.7 (2C, $(CH_2)_2$), 50.6 (2C, $(CH_2)_2$), 52.0 (C1, $CH_2$), 111.6 (1C, CH), 115.7 (1C, CH), 119.2 (1C, CH), 119.7 (1C, qC), 122.5 (1C, $CF_3$), 126.0 (1C, CH), 126.4 (1C, CH), 126.7 (1C, CH), 130.1 (1C, qC), 130.2 (1C, CH), 134.5 (1C, CH), 146.0 (1C, qC), 146.7 (1C, qC), 149.8 (1C, qC), 161.3 (1C, C=O).

El-MS (70 ev): 430 $[M]^+$, 256, 243, 200, 172, 145, 116, 70

Example 8

Preparation of 3-(2-(4-(2,3-dimethylphenyl)piperazine-1-yl)ethyl)-2-ethylquinazoline-4(3H)-one This compound was prepared in compliance with the procedure described in 7d, using 1-(2,3-dimethylphenyl)piperazine instead of 1-(3-(trifluoromethyl)phenyl)piperazine.

El-MS (70 ev): 390 $[M]^+$, 203, 187, 160

Example 9

Preparation of 2-ethyl-3-(2-(4-(2-methoxyphenyl)piperazine-1-yl)ethyl)quinazoline-4(3H)-one This compound was prepared in compliance with the procedure described in 7d, using 1-(2-methoxyphenyl)piperazine instead of 1-(3-(trifluoromethyl)phenyl)piperazine.

El-MS (70 ev): 392 $[M]^+$, 205, 187, 162

Example 10

Preparation of 2-ethyl-3-(2-(4-(2-ethoxyphenyl)piperazine-1-yl)ethyl)quinazoline-4(3H)-one This compound was prepared in compliance with the procedure described in 7d, using 1-(2-ethoxyphenyl)piperazine instead of 1-(3-(trifluoromethyl)phenyl)piperazine.

El-MS (70 ev): 406 $[M]^+$, 219, 187, 176

Example 11

Preparation of 3-(2-(4-(2-chlorophenyl)piperazine-1-yl)ethyl)-2-ethylquinazoline-4(3H)-one This compound was prepared in compliance with the procedure described in 7d, using 1-(2-chlorophenyl)piperazine instead of 1-(3-(trifluoromethyl)phenyl)piperazine.

El-MS (70 ev): 396 $[M]^+$, 223, 200, 195, 173

In vitro affinity assays—$5HT_{1A}$ and $5-HT_{2A}$ receptors

The affinity assays with the $5-HT_{1A}$ and $5-HT_{2A}$ receptors for the compounds addressed by this invention were conducted by the Biochemical and Molecular Pharmacology Laboratory at the Biomedical Science Institute in Rio de Janeiro Federal University (UFRJ), using its own protocols. The development of the experiment protocol to assess compounds with affinity for the $5-HT_{1A}$ receptors was developed on the basis of the experiments conducted by Hall et al (*Journal of Neurochemistry* (1985) 44: 1685-1696); Mongeau et al (*Brain Research* (1992) 590: 229-238) and Peroutka (*Journal of Neurochemistry* (1986) 47: 529-540). The $5-HT_{2A}$ receptors were based on the studies conducted by Johnson et al (*Naunyn-Schmiedeberg's Arch. Pharmacol.* (1996) 354 (2): 205-209); Leysen et al (*Molecular Pharmacology* (1982) 21: 301-314) and Nelson et al (*Journal of Pharmacology and Experimental Therapeutics* (1993) 265: 1272-1279).

The affinity with the $5-HT_{1A}$ receptors was assayed by using 3[H]-8-OH-DPAT (3[H]-8-hydroxy-N,N-dipropyl-2-aminotetraline) (1 nM) as a ligand, and 5-HT (5-hydroxytiptamine—serotonin) (10 μM) as a non-specific ligand. The assay tissue was rat hippocampus.

In order to determine the affinity with the $5-HT_{2A}$ receptors, 3[H]-ketanserin (1 nM) was used as a ligand and ketanserin (1 μM) as a non-specific ligand. The assay tissue was rat cortex. The findings for the affinities are summarized in Tables 1 and 2 below. Table 1 below summarizes the $CI_{50}$ values obtained for the inventive compounds presented in Examples 1 and 8. In order to determine the $CI_{50}$ of these compounds, the inhibition assays were conducted using the compounds at concentrations of 3, 10, 30, 100, 300, 1000 and 3000 nM (in duplicate) for both receptors.

TABLE 1

Determination of the CI$_{50}$ Values.

| Compounds | 5-HT$_{1A}$ CI$_{50}$ (nM) | 5-HT$_{2A}$ CI$_{50}$ (nM) | 5-HT$_{2A}$/5-HT$_{1A}$ CI$_{502A}$/CI$_{501A}$ |
|---|---|---|---|
| Example 1 | 47 | 570 | 12 |
| Example 7 | 253 | 707 | 2.7 |
| Comparative Compound * | 47 | 453 | 9.6 |

* 1,3-Dihydro-1-(2-(4-(3-(trifluoromethyl)phenyl)-1-piperazinyl)ethyl)-2H-benzimidizol-2-one (Flibanserin)

Pursuant to the data presented in Table 1, the inventive compound addressed in Example 1 presented the same CI$_{50}$ value as the comparative compound constituting the state of the art for the 5-HT$_{1A}$ receptor. For the 5-HT$_{2A}$ receptors, the inventive compound addressed in Example 1 presented a value slightly higher than the value obtained for the comparative compounds.

The compound addressed in Example 7 presented a CI$_{50}$ value some five times greater for the 5-HT$_{1A}$ receptors. However, for the 5-HT$_{2A}$ receptors, this compound presented greater affinity than the comparison compound and the compound in Example 1. Although presenting less affinity for the 5-HT$_{1A}$ receptor, this compound demonstrated that it would be interesting as it presented a lower 5-HT$_{2A}$/5-HT$_{1A}$ ratio of interaction on these receptors.

Table 2 presented below summarizes the findings obtained for determining the affinities of the other compounds addressed by this invention. The values presented in the Tables correspond to the assay concentrations of the compounds and the respective inhibition percentages noted.

TABLE 2

Inhibition Percentages

| | 5-HT$_{1A}$ Inhibition Percentage | | | 5-HT$_{2A}$ Inhibition Percentage | | |
|---|---|---|---|---|---|---|
| Compounds | 30 nM | 100 nM | 300 nM | 300 nM | 1000 nM | 3000 nM |
| Example 2 | 21 | 51 | — | 61 | 82 | — |
| Example 3 | 47 | 84 | — | 89 | 88 | — |
| Example 4 | 22 | 84 | — | 48 | 77 | — |
| Example 5 | 12 | 49 | — | 38 | 78 | — |
| Example 6 | 38 | 66 | — | 43 | 63 | — |
| Example 8 | 26 | 76 | 77 | 67 | 86 | 94 |
| Example 9 | 17 | 46 | 69 | 13 | 46 | 78 |
| Example 10 | 26 | 51 | 79 | 8 | 27 | 58 |
| Example 11 | 5 | 26 | 38 | 25 | 52 | 79 |

In Vivo Efficacy Test

In order to determine the in vivo efficacy of the compounds addressed by this invention, the Serotonin Syndrome Model in rats was used. The model was based in the Irwin method (*Psychopharmacologia* (1968), 13: 222-257), adapted to assess the effects of seroton agonists pursuant to Martin et al (*Journal of Pharmacol. Meth.* (1985), 13: 193-200) and Ortman et al (*Naunyn-Schmiedeberg's Arch. Pharmacol* (1981), 316: 225-230).

In the experiment, the compounds being tested were administered to rats (N=6 per group) which were observed in simultaneous comparison with a control group, to which only the excipient was administered as treatment. Two animals from each group were assessed through a series of separate observations. Escitalopram was used as the positive control for the study.

Behavioral and physiological alterations as well as neurotoxicity symptoms, rectal temperature and pupil diameter were recorded.

Additionally, the specific signs related to the stimulation of the 5-HT receptors were observed and quantified, being: head twitches (HT), fore paw treading (FPT), flat body posture (FBP), hind limb splay (HLS), lower lip retraction (LLR) and spontaneous tail flicks (STF) (Straub).

The observations were conducted at 15, 30 and 60 minutes after administration of the compounds being tested.

The compounds were tested as set forth in Examples 1 and 7. As the comparative compound 1,3-dihydro-1-(2-(4-(3-(trifluoromethyl)phenyl)-1-piperazinyl)ethyl)-2H-benzimidizol-2-one (Flibanserin) was used. All the compounds were administered at a dose of 15 mg/kg, intraperitoneal.

The observations of the specific stimulation data of the 5-HT receptors by each compound are presented in the graph given in FIG. 1.

At this dosage, it was possible to note that the compounds presented in Examples 1 and 7 triggered signs of stimulations of the 5-HT receptors. For the compound addressed in Example 1 triggered spontaneous tail flicks (STF), while the compound addressed in Example 7 triggered fore paw treading (FPT) and more spontaneous tail flicks (STF). These two effects are usually triggered by substances that act as 5-HT$_{1A}$ receptor agonists, with their expressions usually attributed to the post-synaptic activation of these receptors. Among the animals tested with the comparison compound constituting the state of the art of this concentration, only one presented signs of stimulation of the 5-HT receptors, which were spontaneous tail flicks.

Although used as therapeutic doses equivalent to those for the comparison substance constituting the state of the art, the compounds addressed by this invention demonstrated greater strength and efficacy when used at the same therapeutic concentration. As these compounds present similar molecular weight, with the lowest molecular weight being that of the comparison compound, this difference may not be simply attributed to the possible the possible molar concentrations employed. If the findings obtained in the in vitro affinity tests are considered, with the 5-HT$_{1A}$ and 5-HT$_{2A}$ receptors, the difference in the effects achieved for the compounds addressed in Examples 1 and 7 are even more striking and unexpected, I contrast to the comparison compound, especially for the compound addressed in Example 7, whose CI$_{50}$ levels are higher than those obtained for the other compounds. Among the hypotheses that might explain this significant activity is the greater power to reach the central nervous system with highly efficacious permeation of the hematoencephalic barrier, or perhaps its activity is due to the lower ratio between the CI$_{50}$ (5-HT$_{2A}$/5-HT$_{1A}$), or possibly a combination of these factors might be responsible for triggering this surprisingly strong effect.

The invention claimed is:

1. A method of treating disorders associated with the 5-HT$_{1A}$ and 5-HT$_{2A}$ serotonin receptors comprising administering to a patient in need thereof a therapeutically effective quantity of a compound of general formula (I):

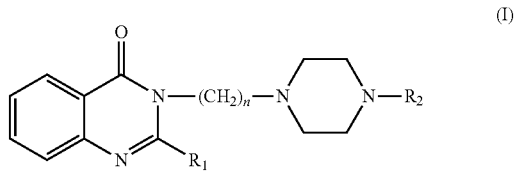

wherein, n=2,

R$_1$ is hydrogen or ethyl, and

R$_2$ is selected from the group consisting of: 3-trifluormethylphenyl, 2-chlorophenyl, 2-methylphenyl, 2,3-dimethylphenyl, 2-cyanophenyl, 2-methoxyphenyl and 2-ethoxyphenyl, or pharmaceutically acceptable salts thereof, wherein said disorder is selected from the group consisting of depression, anxiety, and female sexual dysfunction, wherein said female sexual dysfunction is selected from the group consisting of hypoactive sexual desire disorder, sexual aversion disorder, and female sexual excitation disorder.

2. The method according to claim 1, wherein the therapeutically effective quantity is from about 0.1 mg to about 1,000 mg/day, administered as a single dose or fractioned.

3. The method according to claim 1, wherein the compound is selected from the group consisting of:

3-(2-(4-(3-(trifluoromethyl)phenyl)piperazine-1-yl)ethyl) quinazoline-4(3H)-one;

3-(2-(4-o-tolylpiperazine-1-yl)ethyl)quinazoline-4(3H)-one;

3-(2-(4-(2,3-dimethylphenyl)piperazine-1-yl)ethyl) quinazoline-4(3H)-one;

3-(2-(4-(2-chlorophenyl)piperazine-1-yl)ethyl)quinazoline-4(3H)-one;

3-(2-(4-(2-cyanophenyl)piperazine-1-yl)ethyl)quinazoline-4(3H)-one;

3-(2-(4-(2-methoxyphenyl)piperazine-1-yl)ethyl) quinazoline-4(3H)-one;

2-ethyl-3-(2-(4-(2-trifluoromethyl)phenyl)piperazine-1-yl)ethyl)quinazoline-4(3H)-one;

3-(2-(4-(2,3-dimethylphenyl)piperazine-1-yl)ethyl)-2-ethylquinazoline-4(3H)-one;

3-(2-(4-(2-chlorophenyl)piperazine-1-yl)ethyl)-2-ethylquinazoline-4(3H)-one;

2-ethyl-3-(2-(4-(2-methoxyphenyl)piperazine-1-yl)ethyl) quinazoline-4(3H)-one; and 3-(2-(4-(2-ethoxyphenyl)piperazine-1-yl)ethyl)-2-ethylquinazoline-4(3H)-one.

4. The method according to claim 3, wherein the therapeutically effective quantity is from about 0.1 mg to about 1,000 mg/day, administered as a single dose or fractioned.

5. A method of treating disorders associated with the 5-HT$_{1A}$ and 5-HT$_{2A}$ serotonin receptors comprising administering to a patient in need thereof a therapeutically effective quantity of a composition comprising:

(a) a compound of general formula (I):

(I)

wherein, n=2,

R$_1$ is hydrogen or ethyl and

R$_2$ is selected from the group consisting of: 3-trifluormethylphenyl, 2-chlorophenyl, 2-methylphenyl, 2,3-dimethylphenyl, 2-cyanophenyl, 2-methoxyphenyl and 2-ethoxyphenyl, or pharmaceutically acceptable salts thereof; and (b) a pharmaceutically acceptable excipient, wherein said disorder is selected from the group consisting of depression, anxiety, and female sexual dysfunction, wherein said female sexual dysfunction is selected from the group consisting of hypoactive sexual desire disorder, sexual aversion disorder, and female sexual excitation disorder.

6. The method according to claim 5, wherein the compound is selected from the group consisting of:

3-(2-(4-(3-(trifluoromethyl)phenyl)piperazine-1-yl)ethyl) quinazoline-4(3H)-one;

3-(2-(4-o-tolylpiperazine-1-yl)ethyl)quinazoline-4(3H)-one;

3-(2-(4-(2,3-dimethylphenyl)piperazine-1-yl)ethyl) quinazoline-4(3H)-one;

3-(2-(4-(2-chlorophenyl)piperazine-1-yl)ethyl)quinazoline-4(3H)-one;

3-(2-(4-(2-cyanophenyl)piperazine-1-yl)ethyl)quinazoline-4(3H)-one;

3-(2-(4-(2-methoxyphenyl)piperazine-1-yl)ethyl) quinazoline-4(3H)-one;

2-ethyl-3-(2-(4-(2-trifluoromethyl)phenyl)piperazine-1-yl)ethyl)quinazoline-4(3H)-one;

3-(2-(4-(2,3-dimethylphenyl)piperazine-1-yl)ethyl)-2-ethylquinazoline-4(3H)-one;

3-(2-(4-(2-chlorophenyl)piperazine-1-yl)ethyl)-2-ethylquinazoline-4(3H)-one;

2-ethyl-3-(2-(4-(2-methoxyphenyl)piperazine-1-yl)ethyl) quinazoline-4(3H)-one; and 3-(2-(4-(2-ethoxyphenyl)piperazine-1-yl)ethyl)-2-ethylquinazoline-4(3H)-one.

7. The method according to claim 5, wherein the therapeutically effective quantity is from about 0.1 mg to about 1,000 mg/day of the compound, administered as a single dose or fractioned.

8. The method according to claim 5, wherein the pharmaceutically excipient is selected from the group consisting of diluting agents, binding agents, breakdown agents, anti-clamping agents, lubricants, suspension agents, thickening agents, solvents, surfactants, slip agents, flow agents, coating agents, plastifying agents, sweeteners, isotonicity agents, colorants, conservants, antioxidants, ph control agents, modification agents, complexing agents, flavor masking agents, agents to improve solubility, agents to promote formulation stability, agents to modulate bioavailability, chelating agents, aromatizing agents and flavorizing agents.

* * * * *

UNITED STATES PATENT AND TRADEMARK OFFICE
CERTIFICATE OF CORRECTION

PATENT NO. : 9,169,218 B2  
APPLICATION NO. : 14/227313  
DATED : October 27, 2015  
INVENTOR(S) : Freire Torres Russo et al.

Page 1 of 1

It is certified that error appears in the above-identified patent and that said Letters Patent is hereby corrected as shown below:

On the title page

At item (73) Assignee please change:

"ACHÉ LABORATÓRIOS FARMACÊUTICOS S.A., Sao Paul (BR); ACHÉ INTERNATIONAL (BVI) LTD., Tortola (VG)" to -- ACHÉ LABORATÓRIOS FARMACÊUTICOS S.A., Sao Paulo (BR); ACHÉ INTERNATIONAL (BVI) LTD., Tortola (VG) --

Signed and Sealed this  
Eighth Day of March, 2016

Michelle K. Lee  
*Director of the United States Patent and Trademark Office*